US006814249B2

(12) United States Patent
Lin

(10) Patent No.: US 6,814,249 B2
(45) Date of Patent: Nov. 9, 2004

(54) GARBAGE BIN WITH AIR CLEANER

(76) Inventor: Tsong-Yow Lin, No. 57-1, Yung Ho Street, Yung Ho Village, Ta Tu Hsiang, Taichung Hsien (TW)

(*) Notice: Subject to any disclaimer, the term of this patent is extended or adjusted under 35 U.S.C. 154(b) by 25 days.

(21) Appl. No.: 10/378,303

(22) Filed: Mar. 3, 2003

(65) Prior Publication Data

US 2004/0175303 A1 Sep. 9, 2004

(51) Int. Cl.[7] .............................. B65F 1/00; B65F 1/14; A61L 9/15

(52) U.S. Cl. ................... 220/87.1; 220/908.2; 239/462; 422/186.3

(58) Field of Search ................................ 220/87.1, 745, 220/908, 908.1, 908.2, 909; 239/57, 462, DIG. 23; 422/186.3

(56) References Cited

U.S. PATENT DOCUMENTS 1,327,397 A * 1/1920 Levin ........................ 220/87.1
1,656,015 A * 1/1928 Radcliffe ................... 220/87.1
2,147,139 A * 2/1939 Bigman et al. ............ 220/87.1
2,802,590 A * 8/1957 Tupper ....................... 220/87.1
5,174,462 A * 12/1992 Hames ....................... 220/87.1
6,365,113 B1 * 4/2002 Roberts ................... 422/186.3
6,555,011 B1 * 4/2003 Tribelsky et al. ........ 422/186.3
6,626,316 B2 * 9/2003 Yang .......................... 220/87.1
6,720,950 B2 * 4/2004 Cheng ..................... 422/186.3

FOREIGN PATENT DOCUMENTS

JP 01252401 A * 10/1989 ............. B65F/1/14
JP 05124707 A * 5/1993 ............. B65F/1/14

* cited by examiner

*Primary Examiner*—Sheldon J Richter
(74) *Attorney, Agent, or Firm*—Alan D. Kamrath; Nikolai & Mersereau, P.A.

(57) ABSTRACT

A garbage storage apparatus includes a bin, a cover and an air cleaner. The bin defines a space for storing garbage. The cover is for covering the bin. The air cleaner is communicated with the bin for cleaning air in the bin. The air cleaner may include a catalyst for processing the air. The catalyst may be an optical catalyst that is activated by light.

39 Claims, 11 Drawing Sheets

GARBAGE BIN WITH AIR CLEANER

BACKGROUND OF INVENTION

FIELD OF INVENTION

The present invention relates to a garbage bin capable of cleaning air.

Related Prior Art

Taiwanese Patent Publication No. 483430 discloses a conventional garbage storage apparatus for storing two sorts of garbage. This conventional garbage storage apparatus includes a bin 1 and a holder 2 for holding two bags 3 in the bin 1. The bin 1 includes an upper edge 12 defining an opening. The holder 2 includes a lever 21 and two frames 22. The lever 21 is mounted on an upper edge 12 so as to divide the opening defined in the upper edge 12 into two sub-openings. Bach of the bags 3 is put in the bin 1 through one of the sub-openings. Each of the frames 22 is put in an upper edge of one of the bags 3 and then mounted on the upper edge of the bin 1 and the lever 21. Thus, each of the bags 3 is retained open for taking a type of garbage. In use, one of the bags 3 may store kitchen waste and the other one of the bags 3 other garbage, for example. However, the kitchen waste tends to stink soon after it is put in one of the bags 3.

The present invention is therefore intended to obviate or at least alleviate the problems encountered in the prior art.

SUMMARY OF INVENTION

It is the primary objective of the present invention to provide a garbage storage apparatus for eliminating odor.

According to the present invention, a garbage storage apparatus includes a bin, a cover and an air cleaner. The bin defines a space for storing garbage. The cover is for covering the bin. The air cleaner is communicated with the bin for cleaning air in the bin.

The air cleaner may include a catalyst for processing the air.

The catalyst may be an optical catalyst that is activated by means of light.

Other objectives, advantages, and novel features of the invention will become more apparent from the following detailed description when taken in conjunction with the attached drawings.

BRIEF DESCRIPTION OF DRAWINGS

The present invention will be described through detailed illustration of embodiments referring to the attached drawings wherein.

DETAILED DESCRIPTION OF PREFERRED EMBODIMENT

Figure 1:
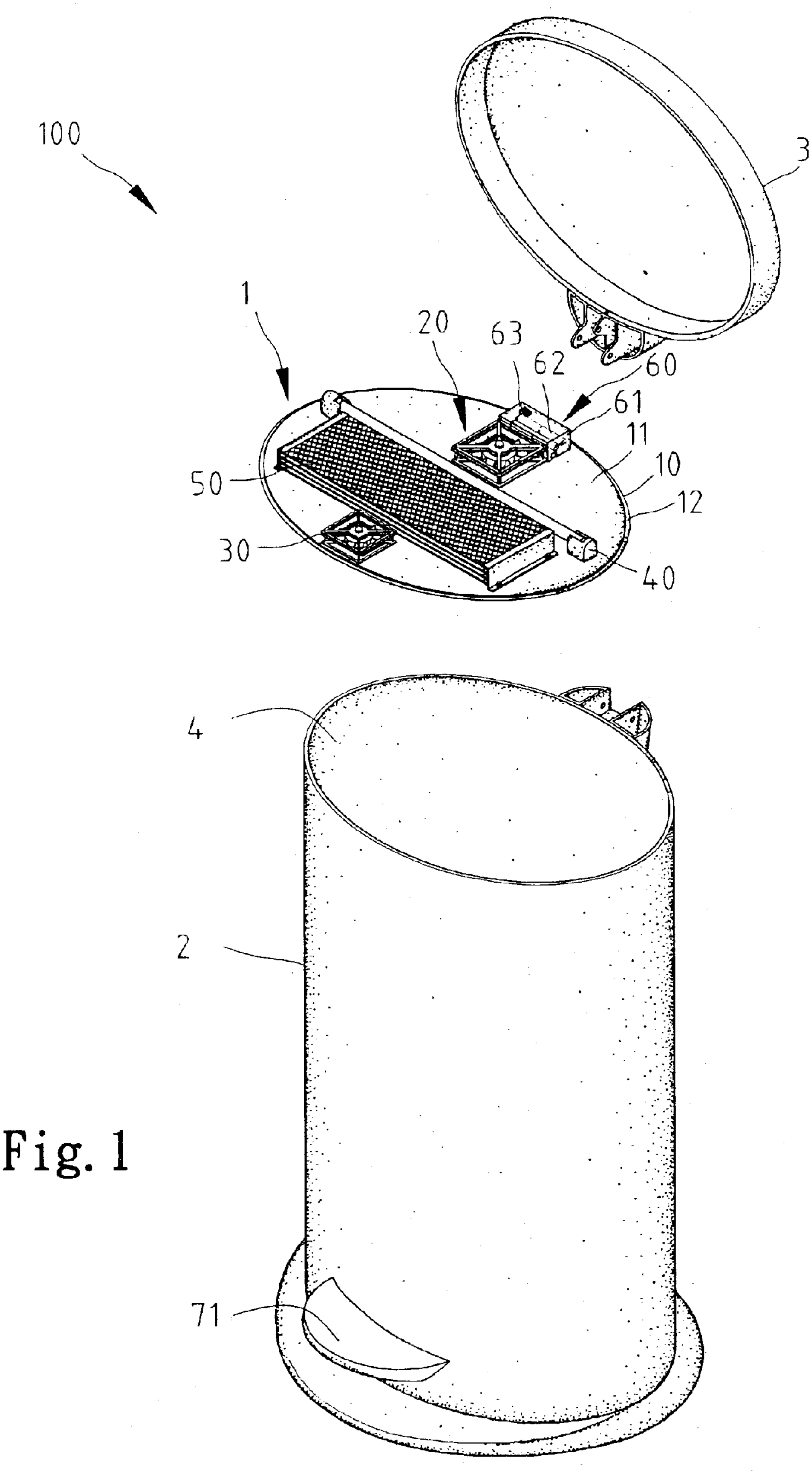
FIG. 1 is an exploded view of a garbage storage apparatus according to a first embodiment of the present invention.
Figure 2:
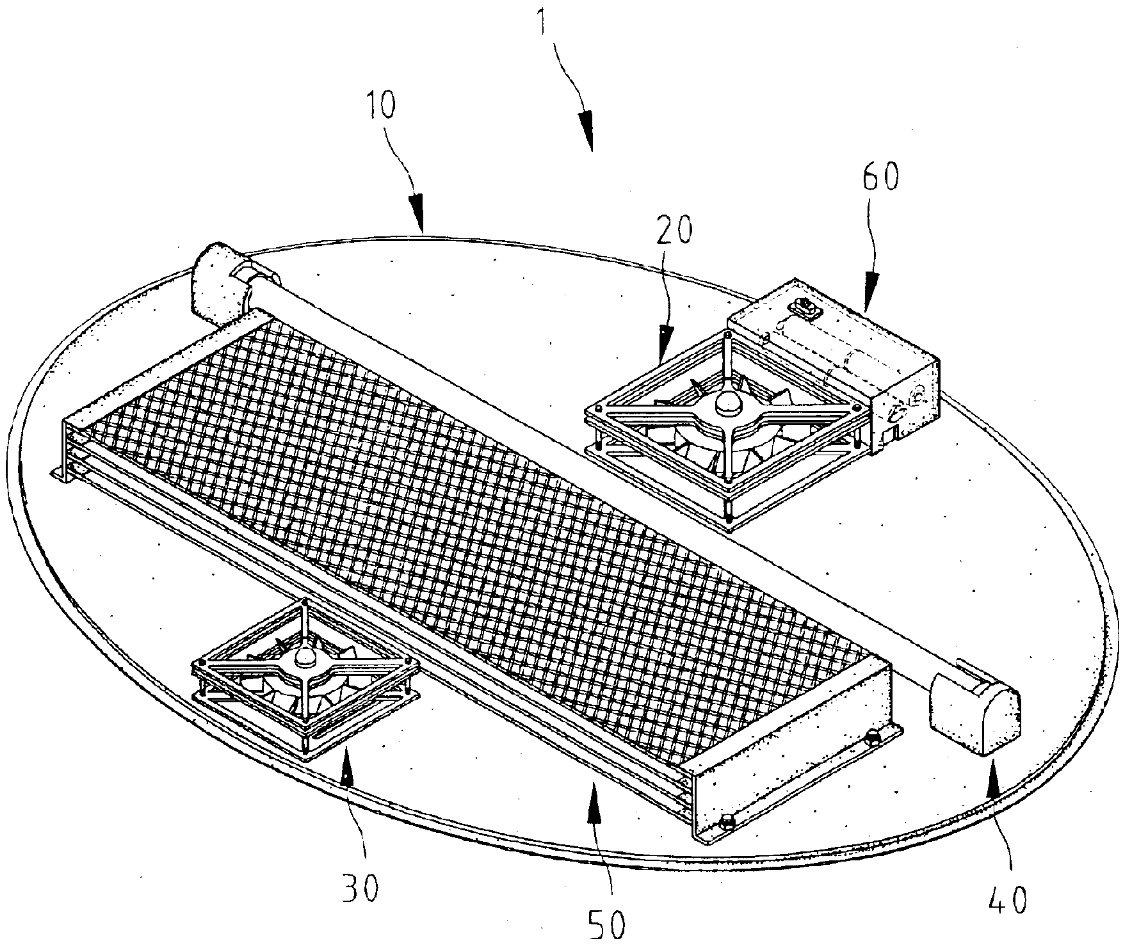
FIG. 2 is a perspective view of an air cleaner used in the garbage storage apparatus shown in FIG. 1.

Referring to FIGS. 1–5, according to a first embodiment of the present invention, a garbage storage apparatus 100 includes a bin 2, a cover 3 pivotally mounted on the bin 2 by a hinge 70 and an air cleaner 1 communicated with the bin 2.

The bin 2 defines a space 4 for receiving garbage 6. In the first embodiment, an internal bin 5 is installed in the space 4. Garbage 6 is to be stored in the internal bin 5. However, the internal bin 5 is optional and can be saved.

The air cleaner 1 includes a support 10, a first fan 20 mounted on the support 10, a second fan 30 mounted on the support 10, a light source 40, an optical catalyst 50 and a power supply 60.

Figure 3:
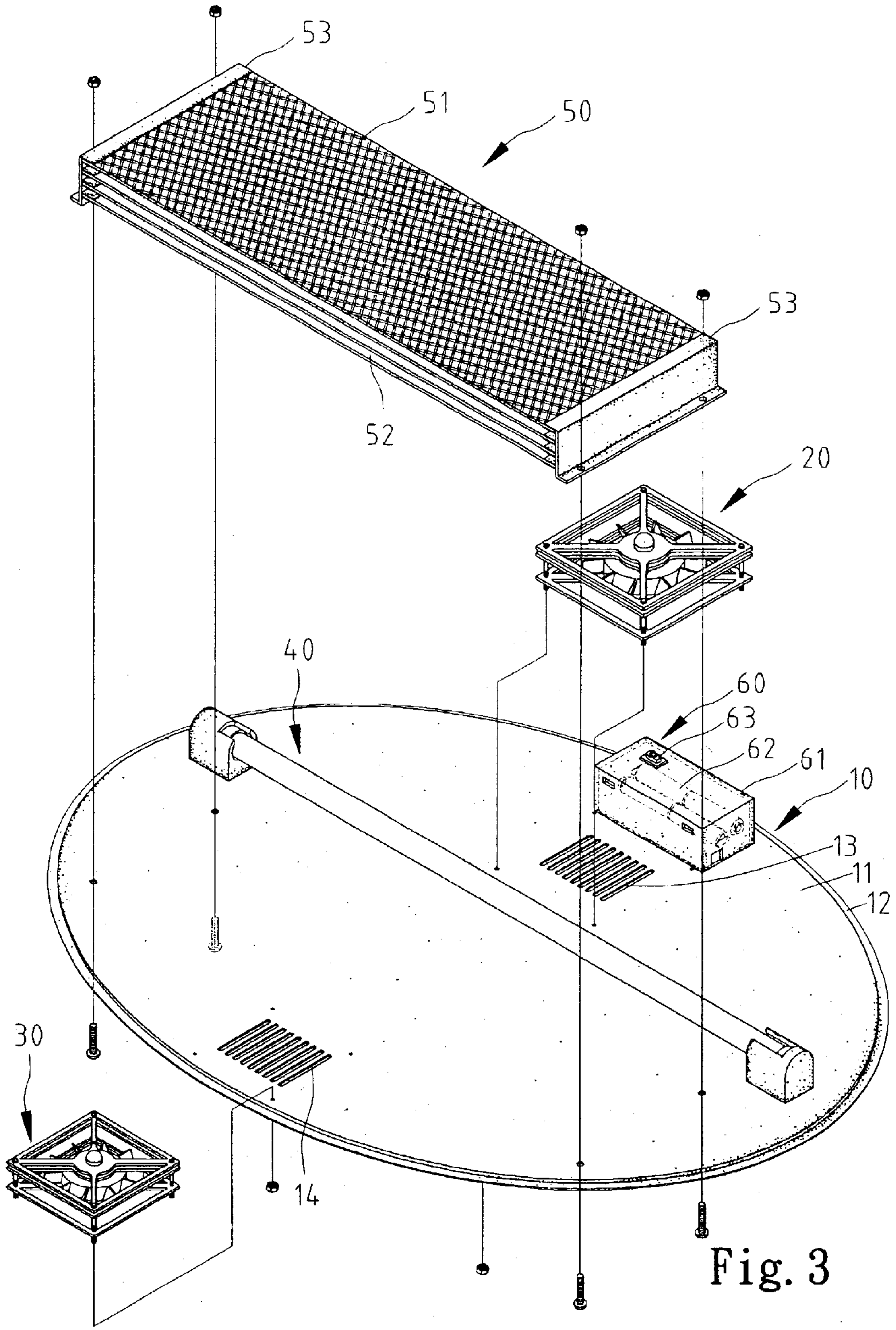
FIG. 3 is an exploded view of the air cleaner shown in FIG. 2.
Figure 4:
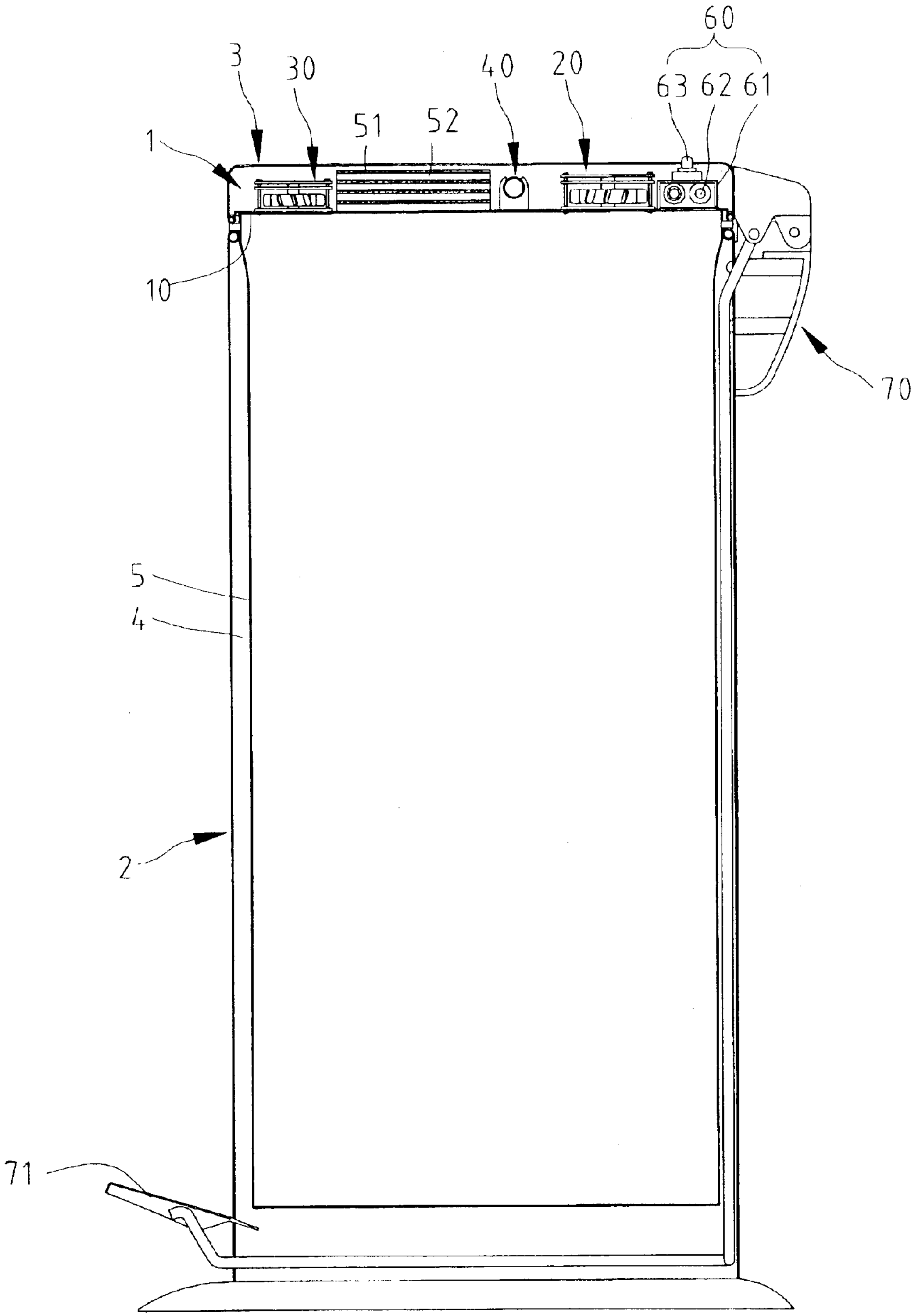
FIG. 4 is a cross-sectional view of the garbage storage apparatus shown in FIG. 1.

Referring to FIG. 3, the support 10 is in the form of a disc with an upper face 11 for supporting the first fan 20, the second fan 30, the light source 40, the optical catalyst 50 and the power supply 60 and with an edge 12 for engagement with an edge of the cover 3. The support 10 defines a first group of slots 13 and a second group of slots 14.

The first fan 20 is secured to the support 10 by means of screws (not numbered). The first fan 20 is located over the first group of slots 13. The first fan 20 can drive air to flow through the first group of slots 13.

The second fan 30 is mounted on the support 10 by means of screws (not numbered). The second fan 30 is located over the second group of slots 14. The second fan 30 can drive air to flow through the second group of slots 14.

A pedal 71 is mounted on the bin 2. The pedal 71 is connected with the cover 30 through a linkage (not shown for being conventional). Thus, the cover 30 can be lifted via treading the pedal 71.

The light source 40 is an ultraviolet light source. The light source 40 is located between the first fan 20 and the second fan 30.

The optical catalyst 50 is secured to the support 10 by means of screws (not numbered). The optical catalyst 50 is located over the light source 40. Moreover, the optical catalyst 50 is located between the first fan 20 and the second fan 30. The optical catalyst 50 includes a plurality of screens 51 held over one another by means of two brackets 53, thus defining a passageway 52 between any two adjacent screens 51 thereof. Each of the screens 51 is coated with an optical catalytic coating of titania. When receiving light from the light source 40, the optical catalytic coatings on the screens 51 act to clean air flowing through the passageways 52.

The power supply 60 includes a box 61 secured to the support 10 by means of screws (not numbered), batteries 62 put in the box 61 for providing direct current to the first fan 20, the second fan 30 and the light source 40 and includes a switch 63 mounted on the box 61 and electrically connected with the batteries 62.

Figure 5:
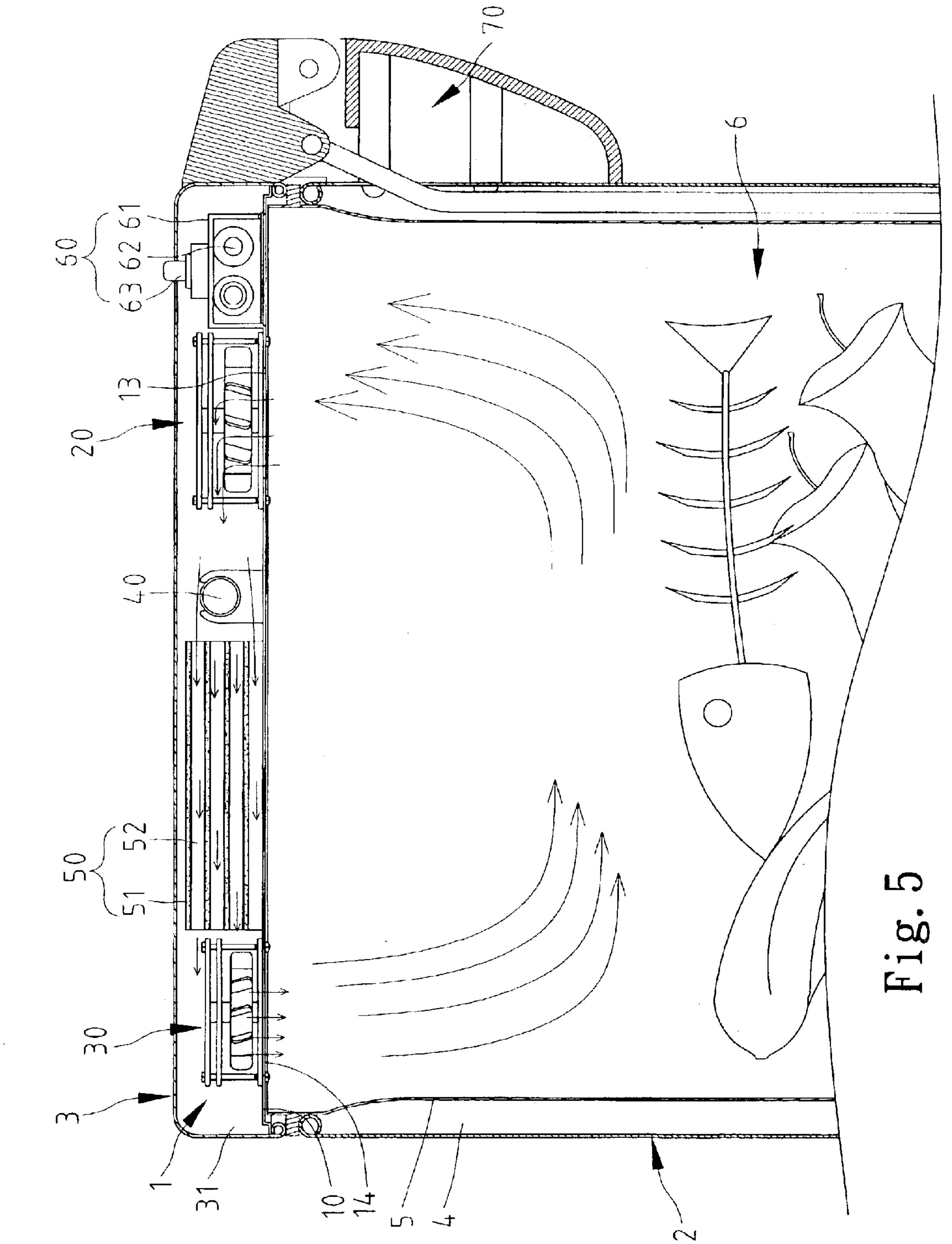
FIG. 5 is a cross-sectional view of a portion of the garbage storage apparatus shown in FIG. 4 in operation.

Referring to FIG. 5, food waste 6 is stored in the bin 2, and the bin 2 is closed by means of the cover 3. The air cleaner 1 is activated. The first fan 20 draws air from a space 4 defined in the internal bin 5 into a space 31 defined between the cover 3 and the support 10. The second fan 30 draws air from the space 31 defined between the cover 3 and the support 10 into the space 4 defined in the internal bin 5. Thus, an air current blows from the first fan 20 to the second fan 3 through the optical catalyst 50. Thus, when flowing through the optical catalyst 50, air mixed with odor coming from the food waste is cleaned by the optical catalyst 50. Therefore, when the cover 3 is lifted, no stinky smell bursts from the bin 2.

Figure 6:
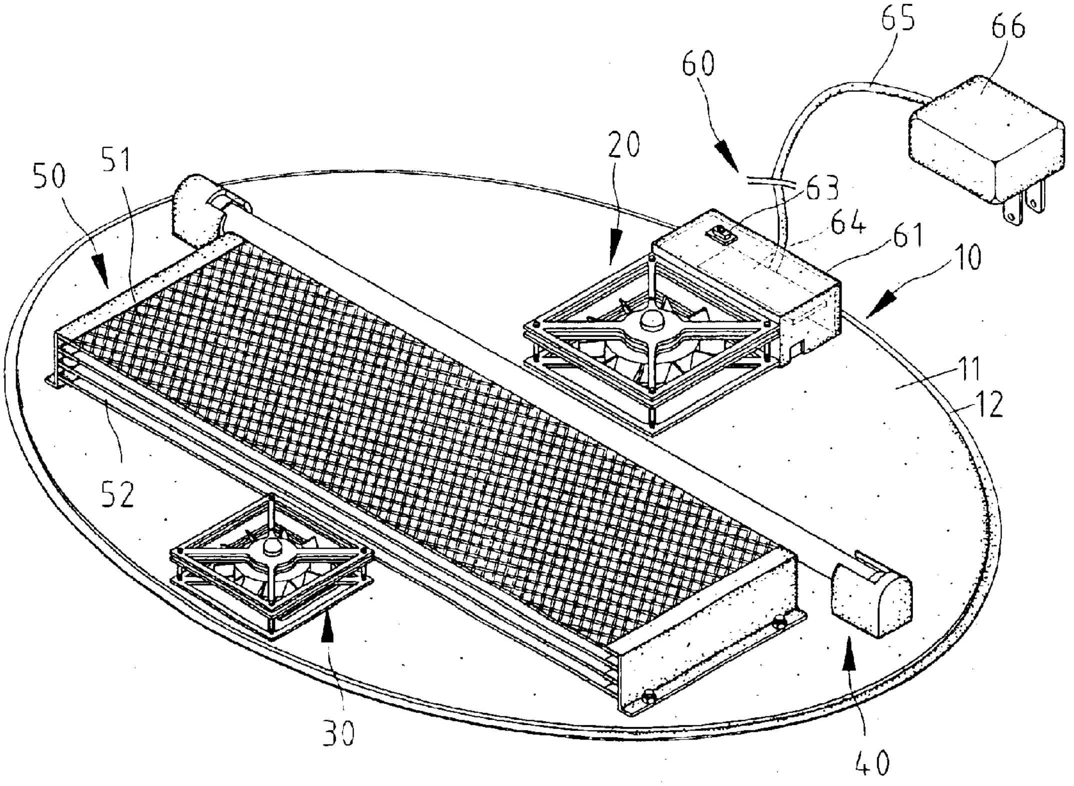
FIGS. 6-11 show second through seventh embodiments of the present invention.

FIG. 6 shows a garbage storage apparatus according to a second embodiment of the present invention. The second embodiment differs from the first embodiment in using an AC power supply 60' instead of the DC power supply 60. The AC power supply 60' includes a box 61, a switch 63 installed on the box 61, a circuit board 64 installed in the box 61, a wire 65 leading from the circuit board 64 and a plug 66 formed at an end of the wire 65.

Figure 7:
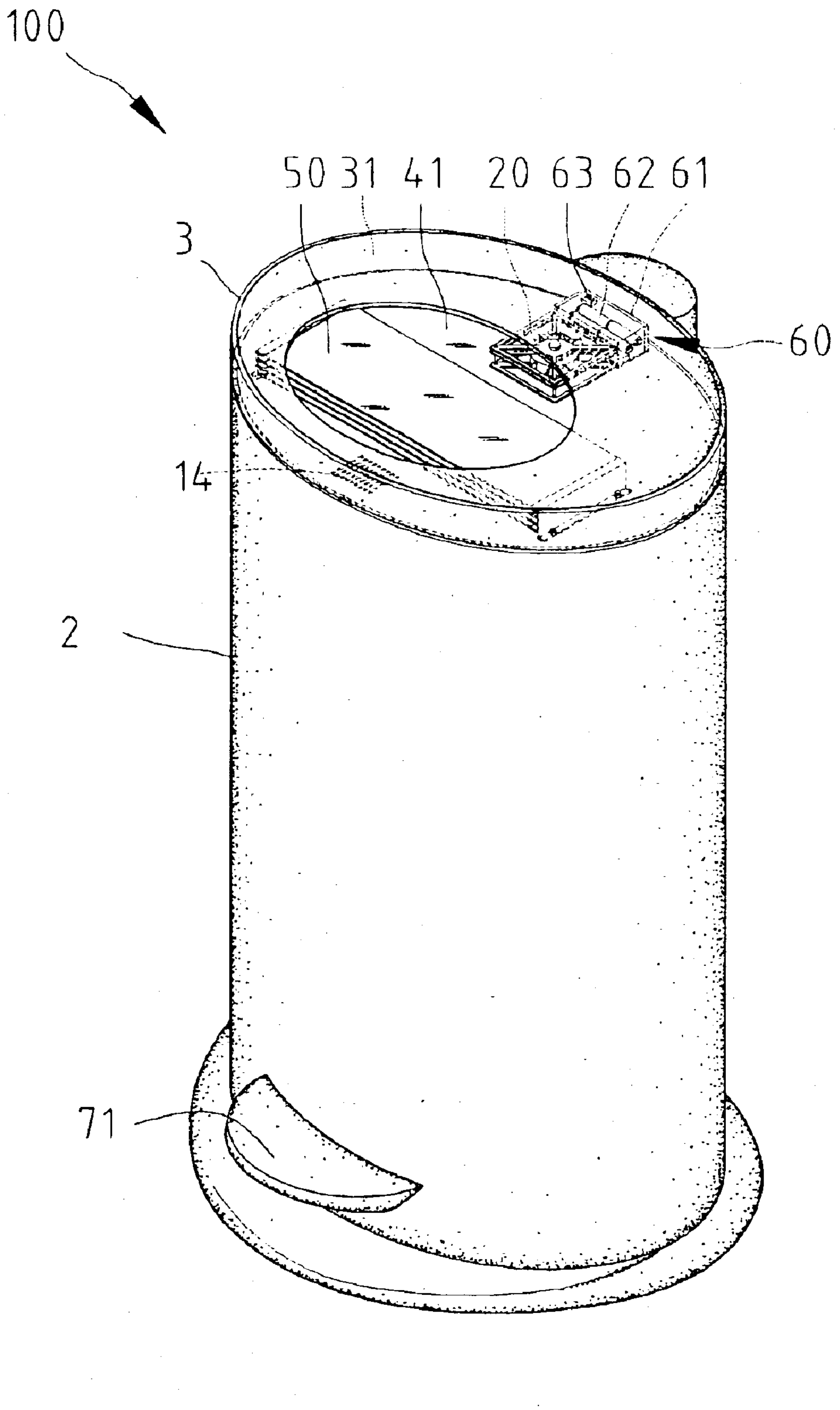

FIG. 7 shows a garbage storage apparatus according to a third embodiment of the present invention. The third embodiment differs from the first embodiment in two aspects. Firstly, the light source 40 is saved. To activate the optical catalyst 50, a window 41 is installed on the cover 3 so that light can shine on the optical catalyst 50 through the window 41. Secondly, the second fan 30 is saved.

Figure 8:
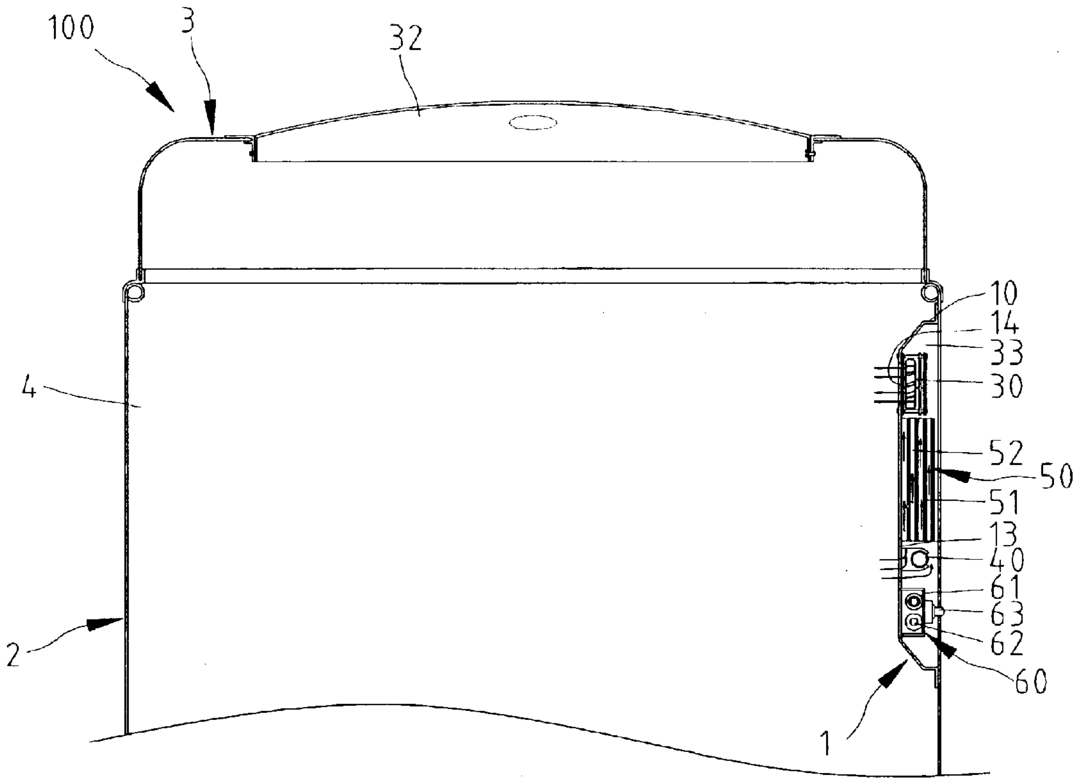

FIG. 8 shows a garbage storage apparatus according to a fourth embodiment of the present invention. The fourth embodiment differs from the first embodiment in two aspects. Firstly, the cover 3 is not pivotally mounted on the bin 2 but simply put on the bin 2. To facilitate lifting of the cover 3, the cover 3 is provided with a handle 32. Secondly, the internal bin 5 is saved, and the air cleaner 1 is located inside of the bin 2. The second fan 30 draws air from a space 33 defined between the bin 2 and the support 10 into the space 4 defined in the bin 2.

Figure 9:
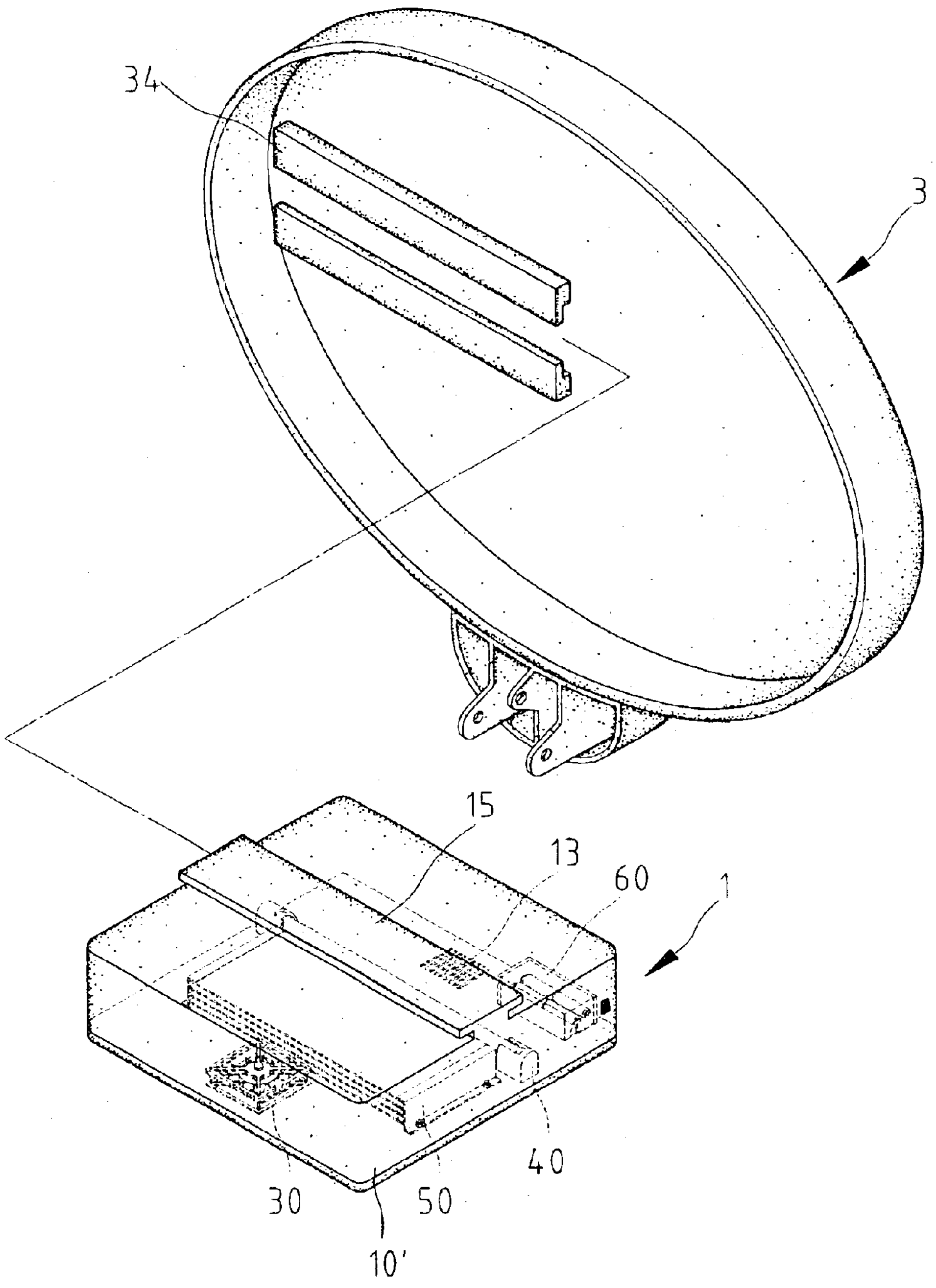

FIG. 9 shows a garbage storage apparatus according to a fifth embodiment of the present invention. The fifth embodiment differs from the first embodiment in two aspects. Firstly, the air cleaner 1 includes a support 10' instead of the support 10. The support 10' is a box in which element are installed. The support 10' includes a connector (not numbered) in the form of a rail for a train. The connector includes a rib (not numbered) formed on the support 10' and two flanges 15 extending from two sides of the rib. The flanges 15 are for sliding engagement with two rails 34 formed on a lower face of the cover 3. Thus, the support 10' is attached to the cover 3 in a releasable manner. Secondly, the air cleaner 1 includes only one fan 30.

Figure 10:
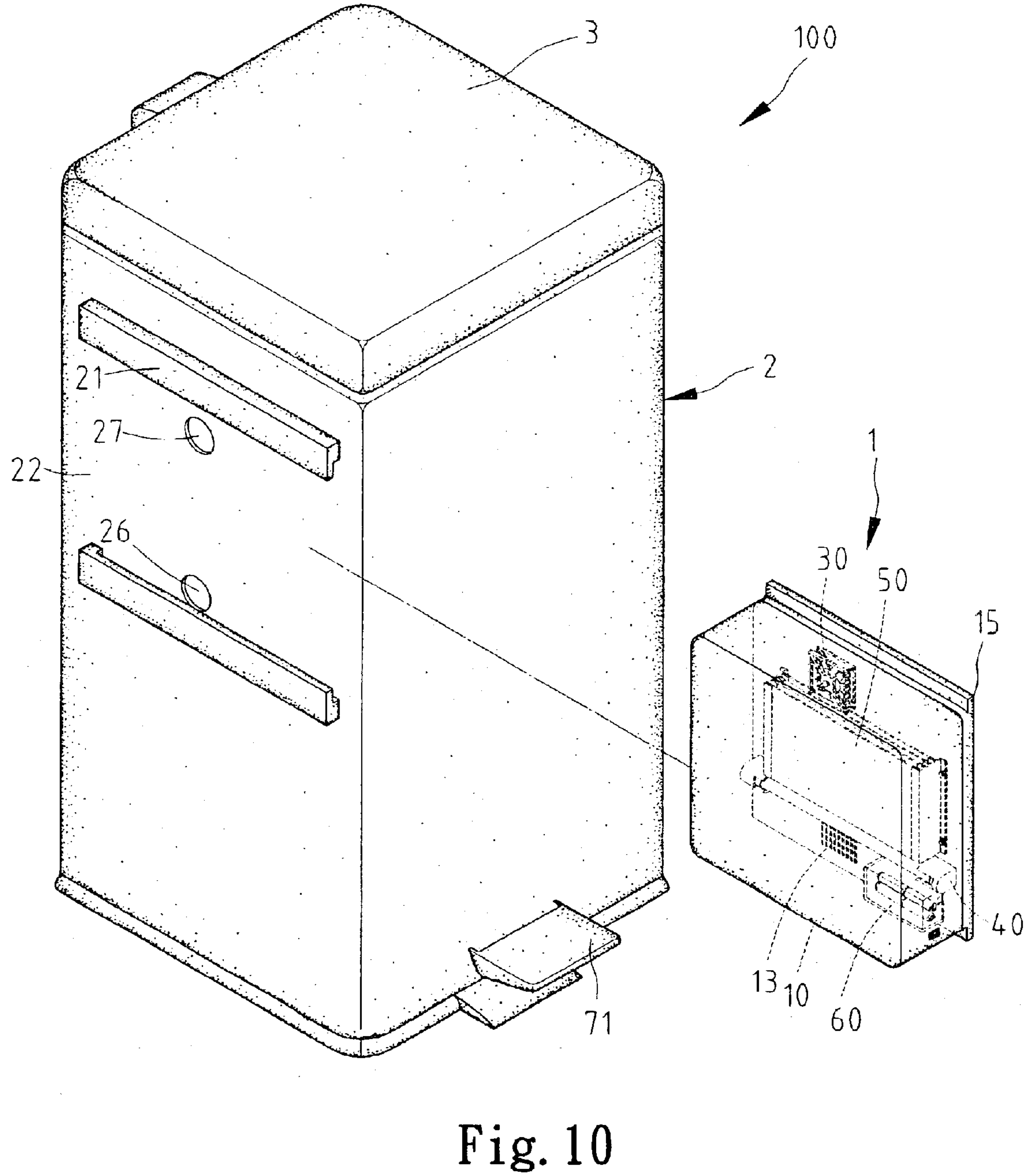

FIG. 10 shows a garbage storage apparatus according to a sixth embodiment of the present invention. The sixth embodiment is similar to the fifth embodiment except for two rails 21 are formed on an outer surface 22 of the bin 2 instead of the rails 34 formed on the cover 3. The bin 2 defines an aperture 26 corresponding to the first group of slots 13 and an aperture 27 corresponding to the second group of slots 14.

Figure 11:
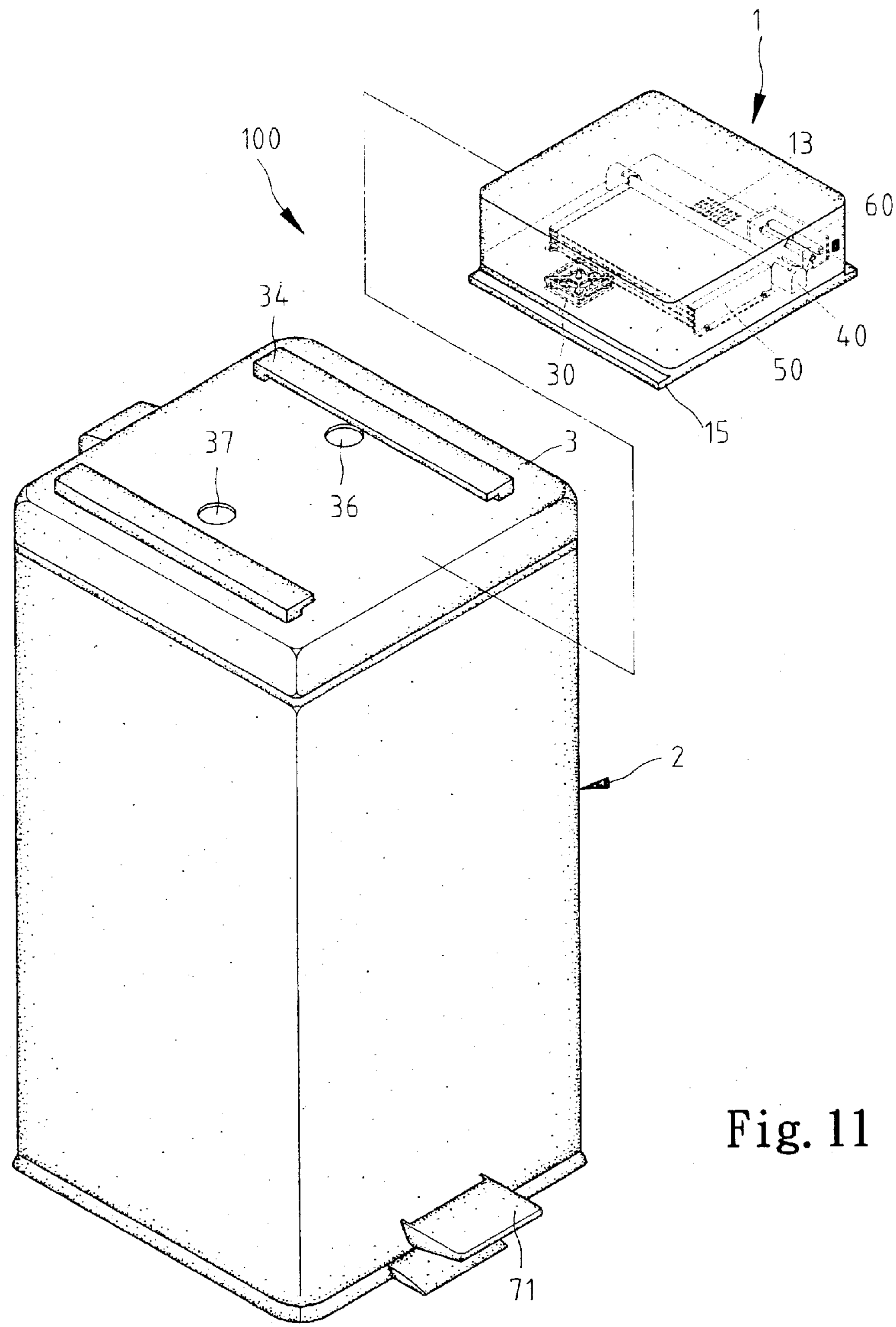

FIG. 11 shows a garbage storage apparatus according to a seventh embodiment of the present invention. The seventh embodiment is similar to the fifth embodiment except for that the rails 34 are formed on an upper face of the cover 3. The cover 3 defines an aperture 36 corresponding to the first group of slots 13 and an aperture 37 corresponding to the second group of slots 14.

The present invention has been described through detailed illustration of the preferred embodiment. Those skilled in the art can derive variations from the preferred embodiment without departing from the scope of the present invention. Therefore, the preferred embodiment shall not limit the scope of the present invention defined in the claims.

What is claimed is:

1. A garbage storage apparatus including:

a bin defining a space for storing garbage;

a cover for covering the bin; and an air cleaner communicated with the bin for cleaning air in the bin, wherein the air cleaner includes a catalyst for processing the air, wherein the catalyst is an optical catalyst that is activated by light.

2. The garbage storage apparatus according to claim 1 wherein the cover is pivotally mounted on the bin.

3. The garbage storage apparatus according to claim 1 including an internal bin installed in the bin for receiving garbage.

4. The garbage storage apparatus according to claim 1 wherein the cover is removed from the bin to allow access to the space for storing garbage and is put on the bin to close the space for storing garbage.

5. The garbage storage apparatus according to claim 4 wherein the cover includes a handle formed thereon.

6. The garbage storage apparatus according to claim 1 wherein the air cleaner is installed in the cover.

7. The garbage storage apparatus according to claim 6 wherein the cover includes a window through which light shines on the optical catalyst.

8. The garbage storage apparatus according to claim 1 wherein the catalyst includes a plurality of screens located over one another, thus defining a passageway between any two adjacent ones thereof.

9. The garbage storage apparatus according to claim 8 wherein each of the screens is coated with an optical catalytic coating.

10. The garbage storage apparatus according to claim 9 wherein the optical catalytic coating is titania.

11. The garbage storage apparatus according to claim 1 including a light source for emitting light to the optical catalyst.

12. The garbage storage apparatus according to claim 11 wherein the light source is an ultraviolet light source.

13. The garbage storage apparatus according to claim 11 including a power supply for powering the light source.

14. The garbage storage apparatus according to claim 13 wherein the power supply is an AC power supply.

15. The garbage storage apparatus according to claim 13 wherein the power supply is a DC power supply.

16. The garbage storage apparatus according to claim 1 wherein the air cleaner is attached to the bin.

17. The garbage storage apparatus according to claim 16 wherein the air cleaner is attached to the bin in a sliding manner.

18. The garbage storage apparatus according to claim 17 wherein the air cleaner includes two flanges formed thereon, and the bin includes two rails formed thereon for engagement with the flanges of the air cleaner.

19. The garbage storage apparatus according to claim 18 wherein the air cleaner is attached to an external face of the bin.

20. The garbage storage apparatus according to claim 19 wherein the air cleaner includes at least one first aperture and at least one second aperture, and the cover defines a first aperture communicated with the first aperture of the air cleaner and an aperture communicated with the second aperture of the air cleaner.

21. The garbage storage apparatus according to claim 1 wherein the air cleaner is attached to the cover.

22. The garbage storage apparatus according to claim 21 wherein the air cleaner is attached to the cover in a sliding manner.

23. The garbage storage apparatus according to claim 22 wherein the air cleaner includes two flanges formed thereon, and the cover includes two rails formed on a lower face thereof for engagement with the flanges of the air cleaner.

24. The garbage storage apparatus according to claim 22 wherein the air cleaner includes two flanges formed thereon, and the cover includes two rails formed on an upper face thereof for engagement with the flanges of the air cleaner.

25. The garbage storage apparatus according to claim 22 wherein the air cleaner includes at least one first aperture and at least one second aperture, and the cover defines a first aperture communicated with the first aperture of the air cleaner and an aperture communicated with the second aperture of the air cleaner.

26. The garbage storage apparatus according to claim 22 wherein the catalyst includes a plurality of screens located over one another, thus defining a passageway between any two adjacent ones thereof.

27. The garbage storage apparatus according to claim 26 wherein each of the screens is coated with an optical catalytic coating.

28. The garbage storage apparatus according to claim 27 wherein the optical catalytic coating is titania.

29. The garbage storage apparatus according to claim 22 including a light source for emitting light to the optical catalyst.

30. The garbage storage apparatus according to claim 29 wherein the light source is an ultraviolet light source.

31. The garbage storage apparatus according to claim 21 wherein the air cleaner includes:

a disc attached to the cover so as to define a space between them, the disc defining at least one first aperture and at least one second aperture; and at least one fan mounted on the disc in order to drive air from the space in the bin to the space between the cover and the disc through the first aperture and from the space between the cover and the disc to the space in the bin through the second aperture.

32. The garbage storage apparatus according to claim 31 wherein the catalyst includes a plurality of screens located over one another, thus defining a passageway between any two adjacent ones thereof.

33. The garbage storage apparatus according to claim 32 wherein the screens are coated with an optical catalytic coating.

34. The garbage storage apparatus according to claim 33 wherein the optical catalytic coating is titania.

35. The garbage storage apparatus according to claim 31 including a light source for emitting light to the optical catalyst.

36. The garbage storage apparatus according to claim 35 wherein the light source is an ultraviolet light source.

37. The garbage storage apparatus according to claim 31 wherein the fan is located over the first aperture.

38. The garbage storage apparatus according to claim 31 wherein the fan is located over the second aperture.

39. The garbage storage apparatus according to claim 31 including a first fan located over the first aperture and a second fan located over the second aperture.

* * * * *